US010406377B2

(12) United States Patent
Kim et al.

(10) Patent No.: US 10,406,377 B2
(45) Date of Patent: Sep. 10, 2019

(54) NEURAL PROBE STRUCTURE COMPRISING COIL EMBEDDED THEREIN AND METHOD FOR MANUFACTURING THE SAME

(71) Applicant: KOREA INSTITUTE OF SCIENCE AND TECHNOLOGY, Seoul (KR)

(72) Inventors: Jinseok Kim, Seoul (KR); Jeiwon Cho, Seoul (KR); Hyungdal Park, Seoul (KR); Yeowool Huh, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 195 days.

(21) Appl. No.: 15/493,302

(22) Filed: Apr. 21, 2017

(65) Prior Publication Data

US 2017/0312535 A1    Nov. 2, 2017

(30) Foreign Application Priority Data

Apr. 27, 2016    (KR) ........................ 10-2016-0051732

(51) Int. Cl.
*A61N 2/00* (2006.01)
*H05K 1/02* (2006.01)
(Continued)

(52) U.S. Cl.
CPC ................ *A61N 2/006* (2013.01); *A61B 5/01* (2013.01); *A61B 5/04001* (2013.01); *A61N 2/02* (2013.01);
(Continued)

(58) Field of Classification Search
CPC .... H01F 5/003; H01F 7/20; H01F 2027/2809; H01F 27/2804; H01F 41/041; A61B 5/01;
(Continued)

(56) References Cited

U.S. PATENT DOCUMENTS 8,277,371 B2    10/2012    Zangen et al.
9,179,875 B2    11/2015    Hua
(Continued)

FOREIGN PATENT DOCUMENTS

KR    10-2007-0005982 A    1/2007
KR    10-0696724 B1    3/2007
(Continued)

OTHER PUBLICATIONS

Chris Hovey et al., "The Guide to Magnetic Stimulation," The Magstim Company Limited, Jul. 2006, United Kingdom, pp. 1-45.
(Continued)

*Primary Examiner* — Christine H Matthews
*Assistant Examiner* — Joshua Daryl D Lannu
(74) *Attorney, Agent, or Firm* — NSIP Law

(57) ABSTRACT

A neural probe structure includes a probe which is inserted into a living body, and a magnetic field inductor which is formed in the probe, wherein when a power source is supplied, the magnetic field inductor generates a magnetic field and applies magnetic stimulation to a target site of the living body into which the probe is inserted. A method for manufacturing the neural probe structure includes forming a first pattern on a first substrate and filling the first pattern with a conductor, stacking a second substrate on the first substrate, and forming a second pattern connected to the first pattern on the second substrate and filling the second pattern with a conductor, wherein the first substrate and the second substrate form the probe, and the conductor of the first pattern and the conductor of the second pattern form the magnetic field inductor.

17 Claims, 8 Drawing Sheets

(51) Int. Cl.
- *H01F 41/04* (2006.01)
- *H01F 27/28* (2006.01)
- *A61N 2/02* (2006.01)
- *A61B 5/04* (2006.01)
- *H05K 1/16* (2006.01)
- *A61B 5/01* (2006.01)
- *H01F 5/00* (2006.01)
- *H01F 7/20* (2006.01)

(52) U.S. Cl.
CPC ............ *H01F 5/003* (2013.01); *H01F 7/20* (2013.01); *H01F 27/2804* (2013.01); *H01F 41/041* (2013.01); *H05K 1/0265* (2013.01); *H01F 2027/2809* (2013.01); *H05K 1/165* (2013.01)

(58) Field of Classification Search
CPC .. A61B 5/04001; H05K 1/0265; H05K 1/165; A61N 2/02; A61N 2/006
See application file for complete search history.

(56) References Cited

U.S. PATENT DOCUMENTS

2006/0173259 A1* 8/2006 Flaherty ............... A61B 5/0031
600/331
2006/0265022 A1* 11/2006 John .................. A61B 5/14553
607/45
2013/0131485 A1 5/2013 Oh et al.
2015/0112359 A1 4/2015 Gillbe

FOREIGN PATENT DOCUMENTS

KR   10-2013-0057246 A   5/2013
WO   WO 2014/197435 A1   12/2014

OTHER PUBLICATIONS

F S Salinas et al., "Detailed 3D models of the induced electric field of transcranial magnetic stimulation coils," Physicians in Medicine and Biology, May 2007, vol. 52, pp. 2879-2892.

Hadass Tischler et al., "Mini-coil for magnetic stimulation in the behaving primate," Journal of Neuroscience Methods, vol. 194, 2011, pp. 242-251.

* cited by examiner

NEURAL PROBE STRUCTURE COMPRISING COIL EMBEDDED THEREIN AND METHOD FOR MANUFACTURING THE SAME

CROSS-REFERENCE TO RELATED APPLICATION

This application claims priority to Korean Patent Application No. 10-2016-0051732, filed on Apr. 27, 2016, and all the benefits accruing therefrom under 35 U.S.C. § 119, the contents of which in its entirety are herein incorporated by reference.

BACKGROUND

1. Field

The present disclosure relates to a neural probe structure and a method for manufacturing the same, and more particularly, to a neural probe structure that is inserted into a human body to stimulate the nerves in the inserted body part by a magnetic field, and obtain signals generated from the stimulated nerves, and a method for manufacturing the same.

[Description about National Research and Development Support]

This study was supported by the Global Frontier Project of Ministry of Science, ICT and Future Planning, Republic of Korea (Project No. 1711025644) under the superintendence of National Research Foundation of Korea.

2. Description of the Related Art

Recently, to treat various brain diseases and understand the working mechanism of the brain, studies on technology to stimulate the cranial nerves with various stimulation means, and sense and analyze neural signals emitted from the cranial nerves due to the stimulation are being actively made.

Methods for stimulating the cranial nerves include electrical stimulation to stimulate the cranial nerves by applying an electric current, drug stimulation to stimulate the cranial nerves by injecting a fluid, optical stimulation to stimulate the cranial nerves with optical radiation, and magnetic stimulation to stimulate the cranial nerves by changing the strength of a magnetic field. The cranial nerves in a target site are artificially stimulated using the stimulation means, and in response, neural signals are emitted from the cranial nerves and collected.

Among the cranial nerve stimulation means, electrical stimulation, drug stimulation, and optical stimulation stimulates the cranial nerves by directly inserting a neural probe manufactured to a small scale via micromachining technique into the brain, to transmit each stimulation medium without causing great damage when inserted into the brain.

The electrical stimulation stimulates the cranial nerves by emitting electrical signals from electrodes connected up to the distal end of the neural probe. The drug stimulation stimulates the cranial nerves by injecting drugs into the brain through microfluidic channels formed in the neural probe. The optical stimulation stimulates the cranial nerves with light irradiation into the brain through an optical waveguide provided in the neural probe. As described above, it is possible to directly stimulate a target site through the neural probe inserted into the brain.

However, in the case of electrical stimulation, localizing stimulation of the cranial nerves is difficult because a material itself of which the brain is made is conductive, and there is a risk of damage to the cranial nerves. Furthermore, in the case of optical stimulation, stimulation of the cranial nerves with light irradiation requires transfection of specific genes that are activated and deactivated by a specific wavelength of light, leaving problems to be solved for future clinical applications.

On the other hand, among the conventional stimulation means, magnetic stimulation stimulates the cranial nerves from outside the skull through a magnetic stimulation device formed of a metal coil without insertion into the brain or other surgeries. The conventional magnetic stimulation has an advantage in stimulating the cranial nerves without causing damage to the brain.

However, because the conventional magnetic stimulation stimulates the cranial nerves by applying a magnetic field from outside the skull, localizing the stimulation of cranial nerves to a specific target site is very difficult. Especially, in the case of cranial nerve stimulation of deep brain regions, it is more difficult to increase focality of the magnetic stimulation.

Accordingly, there is a growing need for magnetic stimulation means for localizing stimulation of the cranial nerves to increase focality while minimizing cranial nerve damage caused by stimulation, and a method for manufacturing the same.

SUMMARY

The present disclosure is directed to providing a neural probe structure in which a probe comprising a conducting coil embedded therein is inserted into a body, an electric current is applied to the coil to generate a magnetic field, magnetic stimulation is delivered locally to the inserted body part, and response signals are collected, and a method for manufacturing the same.

To achieve the object, a neural probe structure according to an embodiment of the present disclosure includes a probe which is inserted into a living body, and a magnetic field inductor which is formed in the probe, wherein when a power source is supplied, the magnetic field inductor generates a magnetic field and applies magnetic stimulation to a target site of the living body into which the probe is inserted.

According to an embodiment of the present disclosure, the magnetic field inductor may be a coil.

According to an embodiment of the present disclosure, the coil may be placed such that an axial direction of the coil is parallel to an insertion direction of the probe.

According to an embodiment of the present disclosure, the coil may be placed such that an axial direction of the coil is perpendicular to an insertion direction of the probe.

According to an embodiment of the present disclosure, the coil may be a rectangular coil.

According to an embodiment of the present disclosure, a pair of magnetic field inductors placed close to each other may be included, and each magnetic field by the pair of magnetic field inductors may reinforce each other at the target site.

According to an embodiment of the present disclosure, the magnetic field inductors may be a pair of coils whose axial directions are parallel to each other, and directions of each magnetic field by the pair of coils may be opposite to each other with respect to the axial direction, so that the magnetic fields reinforce each other at the target site in front of an open end of the pair of coils.

According to an embodiment of the present disclosure, a plurality of magnetic field inductors placed apart in a lengthwise direction of the probe may be included.

According to an embodiment of the present disclosure, an electrode array may be provided in the probe to obtain a neural signal generated in response to the magnetic stimulation.

According to an embodiment of the present disclosure, the probe may include a temperature sensor array to measure temperature in the living body.

To achieve the object, a method for manufacturing a neural probe structure according to another embodiment of the present disclosure includes forming a first pattern on a first substrate and filling the first pattern with a conductor, stacking a second substrate on the first substrate, and forming a second pattern connected to the first pattern on the second substrate and filling the second pattern with a conductor, wherein the first substrate and the second substrate form the probe, and the conductor of the first pattern and the conductor of the second pattern form the magnetic field inductor.

According to an embodiment of the present disclosure, the magnetic field inductor may be formed in a shape of a coil.

According to an embodiment of the present disclosure, the conductor of the first pattern may be a first turn of the coil of an open loop type, the conductor of the second pattern may be a pillar extending upwards from one end of the first turn, and the method may further include stacking one or more substrates including one of remaining turns of the coil of an open loop type and pillars electrically connecting each turn in an alternating manner on the second substrate in a sequential order, to form a coil whose axial direction is placed perpendicular to an insertion direction of the probe.

According to an embodiment of the present disclosure, the conductor of the first pattern may be base of each turn of the coil, the conductor of the second pattern may be pillars each extending upwards from two ends of the base of each turn, and the method may include stacking a third substrate including top of each turn of the coil connecting one side pillar of one turn of two adjacent turns to the other side pillar of the other turn on the second substrate, to form a coil whose axial direction is placed parallel to an insertion direction of the probe.

DETAILED DESCRIPTION

Figure 1:
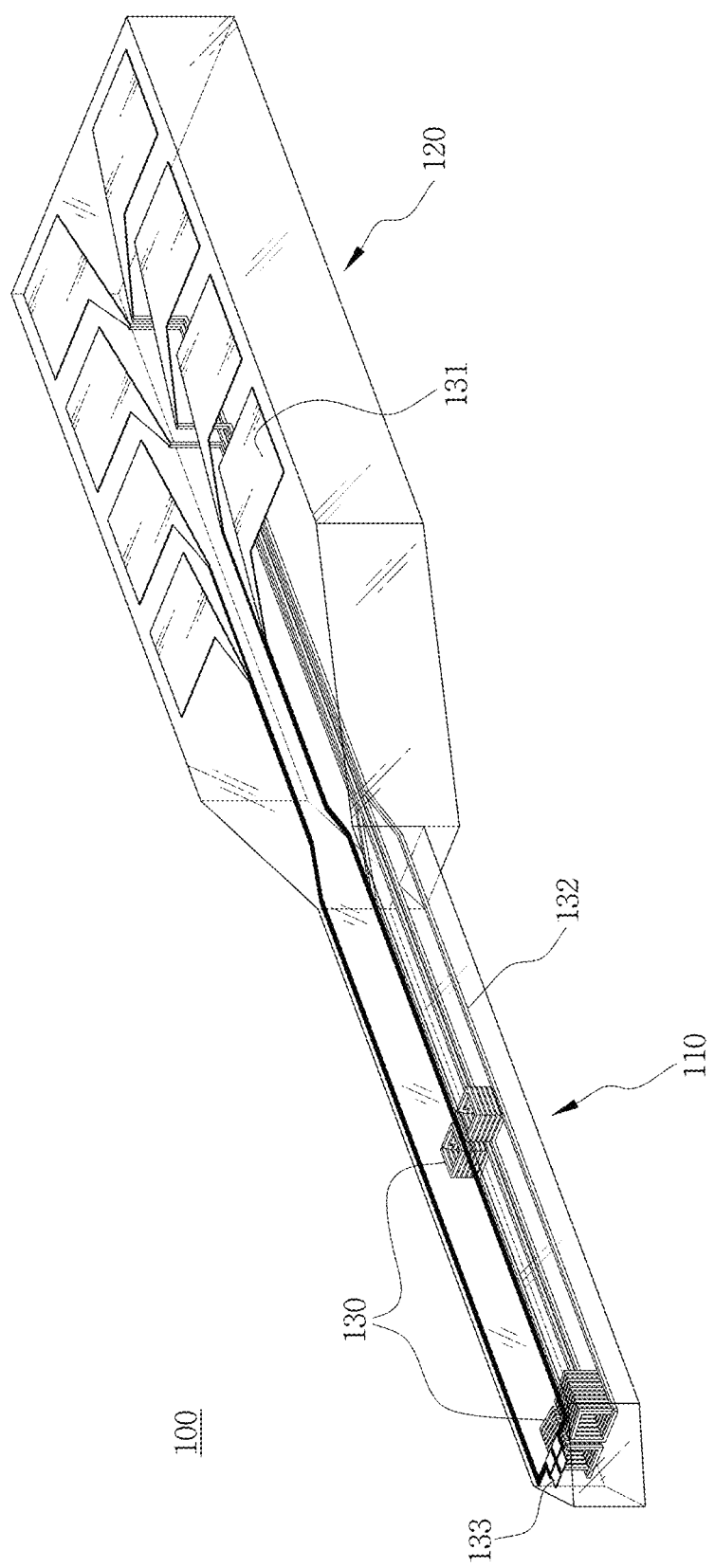
FIG. 1 is a schematic perspective view of a neural probe structure according to an embodiment of the present disclosure.

Advantages and features of the present disclosure, and methods for achieving the same will be apparent from the embodiments described below with reference to the accompanying drawings. However, the present disclosure is not limited to the embodiments set forth therein and will be embodied in different forms, and these embodiments are provided so that the present disclosure will be thorough and complete, and will fully convey the scope of the present disclosure to those skilled in the art, and the present disclosure is only defined by the appended claims.

The shape, size, ratio, angle, and number disclosed in the drawings to describe the embodiments of the present disclosure is for illustration only, and the present disclosure is not limited to the illustration. Furthermore, in describing the present disclosure, when details of relevant known technology are deemed to make the essence of the present disclosure ambiguous, its detailed description is omitted herein. Unless 'only' is stated herein, 'including', 'having', and 'comprising' as used herein includes any additional component. Unless otherwise expressly provided herein, the singular forms include the plural forms.

The components are interpreted as having tolerances unless otherwise specified.

In the case of a description of a positional relationship, for example, 'on', 'above', 'below', and 'beside' that expresses a positional relationship between two parts, one or more other parts may be disposed between the two parts unless 'immediately' or 'directly' is used herein.

It will be understood that when an element or layer is referred to as being "on" another element or layer, it can be directly on the other element or layer or intervening elements or layers may be present. Like reference numerals denote like components throughout the drawings.

Although the terms first, second, etc. are used to narrate various components, it is obvious that these components are not confined by the terms. These terms are only used to distinguish one component from another. Accordingly, it is obvious that a first component stated hereinafter may be a second component within the technical spirit of the present disclosure.

The size and thickness of each component illustrated in the drawings is shown for convenience of description, and the present disclosure is not limited to the size and thickness of the components as shown.

Each feature of many embodiments of the present disclosure may be connected or combined with each other in part or in whole, and as fully understood by those skilled in the art, various interactions and operations can be technically accomplished, and each embodiment may work independently from each other and may work together in correlation.

Hereinafter, a neural probe structure according to an embodiment of the present disclosure will be described with reference to the accompanying drawings.

Referring to FIG. 1, the neural probe structure 100 according to an embodiment of the present disclosure includes a probe 110 and a body 120.

The probe 110 is a part that is inserted into a living body, for example, a human body. The probe 110 may be manufactured with a suitable length to deliver magnetic stimulation from a distal end of the probe 110 to a corresponding site in consideration a distance from the skin surface to the site at a maximum depth where stimulation is required. Furthermore, the probe 110 is preferably as thin as possible in consideration its material and length, in order to get less vulnerable to break and minimize damage to the human body when inserted. On the other hand, sharpening the distal end of the probe 110 that is inserted into the body for the first time is advantageous in terms of minimize pain through smooth insertion.

The probe 110 is fixed to the body 120. The probe 110 is formed such that a proximal end is fixed to the body 120 and a distal end protrudes from the body 120. The probe 110 may be integrally formed with the body 120. Furthermore, the probe 110 and the body 120 may be formed from polymer material.

At least one coil 130 is formed in the probe 110. The coil 130 generates a magnetic field when a power source is supplied. The coil 130 is advantageous in terms of controlling the magnitude of the magnetic field by adjusting the intensity of the electric current and the number of turns of the coil 130. Rather, it should be noted that the probe 110 may be equipped with magnetic field inductors of various shapes other than the coil 130 to apply magnetic stimulation to the target site of the body into which the probe 110 is inserted.

The coil 130 may be placed at the distal end of the probe 110. As the probe 110 is inserted into the body, the coil 130 is disposed adjacent to the target site or in the target site. As power is supplied to the coil 130 with the probe 110 inserted into the body, a magnetic field generated by the coil 130 stimulates the target site.

The coil 130 may be placed between the distal end and the proximal end of the probe 110. Thereby, besides the distal end of the probe 110, the target site at a shallower depth may be stimulated at the same time. In this instance, stimulation means of a different scheme may be provided at the distal end of the probe 110, and multiple coils 130 may be placed at multiple locations on the probe 110 as described below.

When an electric current flows in the coil 130, a magnetic field is formed around the coil 130. The direction of the magnetic field changes depending on the direction of the electric current flowing in the coil 130 and the direction in which the coil 130 is wound. Generally, a magnetic field is formed, starting from one open end of the coil 130 turning back to the other open end. The magnetic field by the coil 130 may be formed at various angles along the axial direction of the coil 130 placed in the probe 110.

Figure 2:
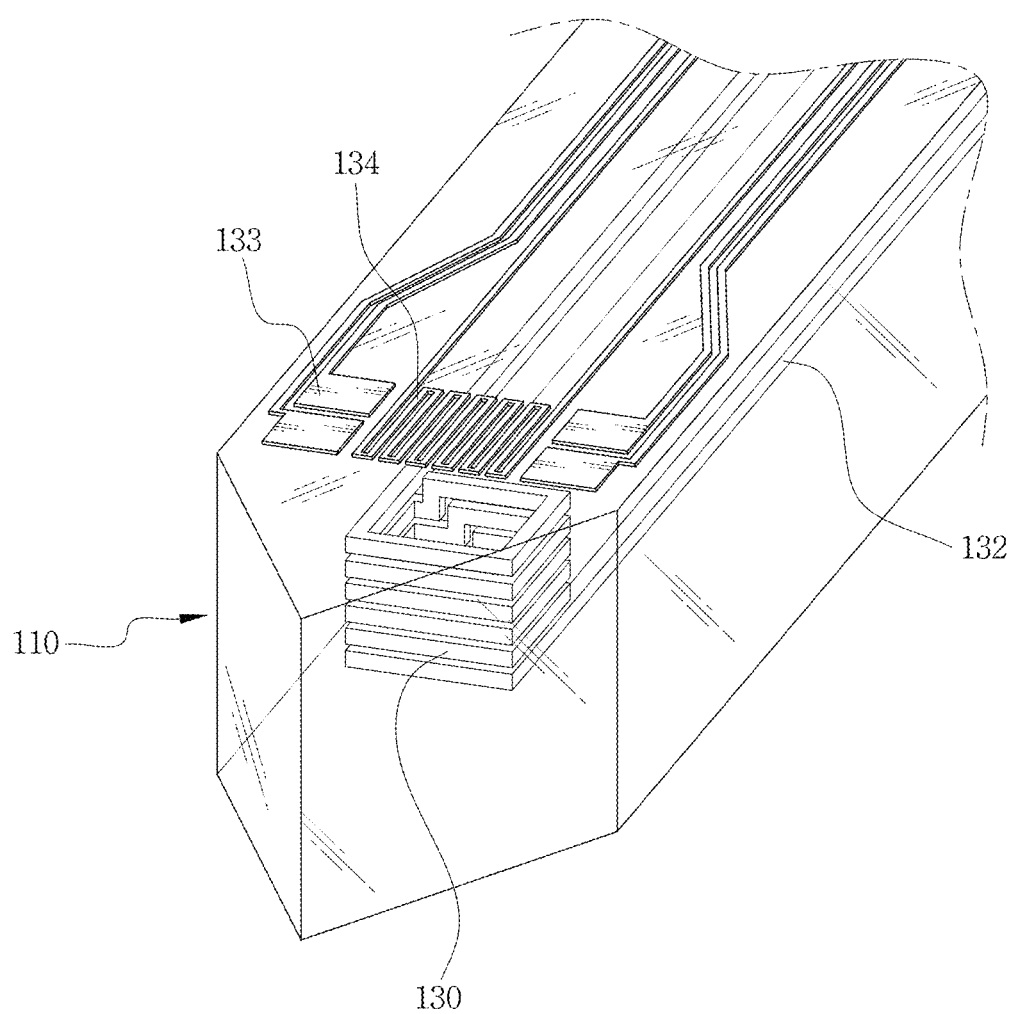
FIG. 2 is a partially enlarged perspective view schematically showing an example of a neural probe structure with one coil placed perpendicular to an insertion direction of a probe.
Figure 3:
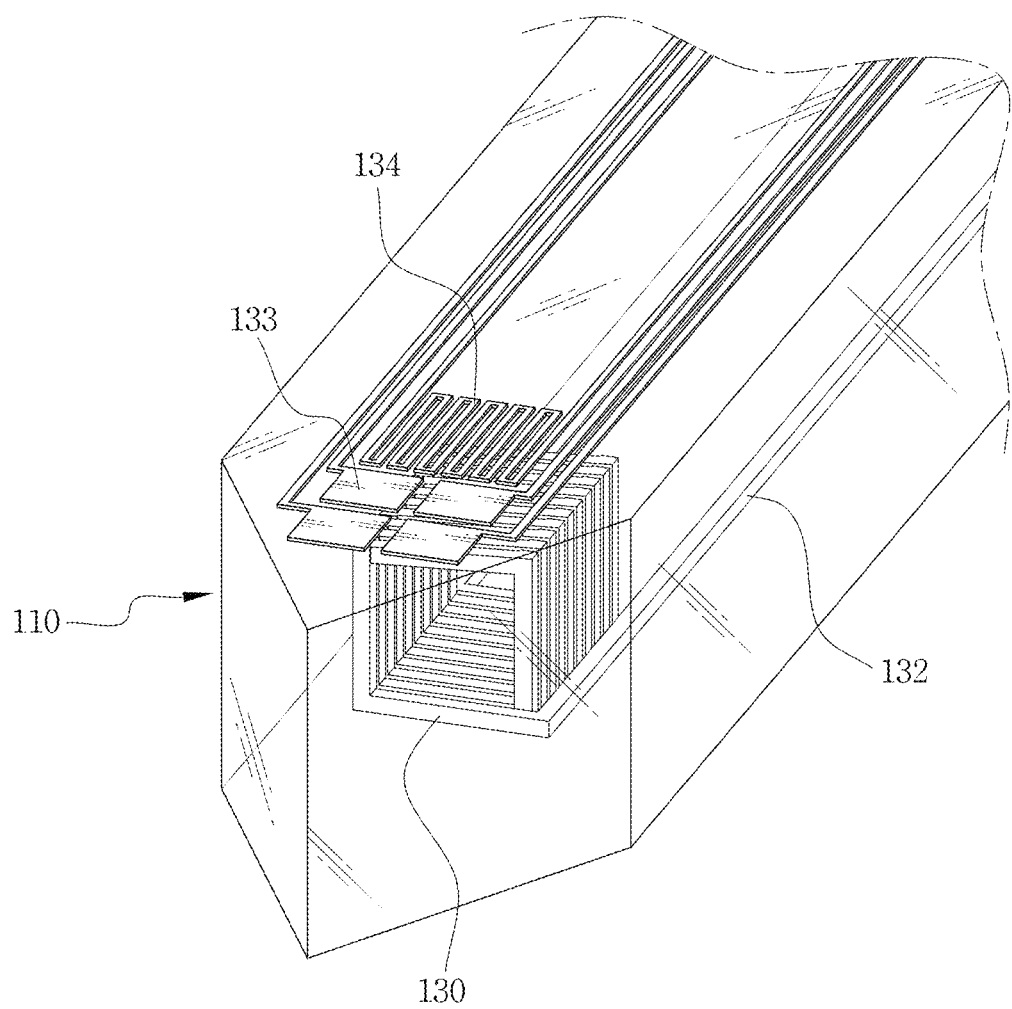
FIG. 3 is a partially enlarged perspective view schematically showing an example of a neural probe structure with one coil placed parallel to an insertion direction of a probe.

The coil 130 can be placed in the probe 110 at various angles, but because it is manufactured to a small scale, placing the coil 130 whose the axial direction is perpendicular to the insertion direction of the probe 110 as shown in FIG. 2 or parallel to the insertion direction of the probe 110 as shown in FIG. 3 is advantageous in terms of yield.

First, the vertical coil 130 may be placed such that two open ends of the coil 130 having relatively strong magnetic field strength are close to the target site on the two sides, when inserted. Due to the thickness of the probe 110, the vertical coil 130 may have a relatively small number of turns. In this regard, the vertical coil 130 is suitable when magnetic stimulation is delivered to a wide target site by a relatively weak strength of magnetic field.

On the other hand, the horizontal coil 130 is placed such that one of two open ends of the coil having relatively strong magnetic field strength is close to the target site along the insertion direction, when inserted. The other open end of the coil 130 is placed relatively far from the target site. On the other hand, in design, the horizontal coil 130 is relatively easy to increase or decrease the number of turns of the coil 130, so it is suitable for intensively delivering magnetic stimulation to a relatively narrow target site with various strengths of magnetic field such as stronger or weaker magnetic field to the target site.

The multiple coils 130 may be placed at the probe 110. As previously described, the coils 130 may be placed at multiple location on the probe 110. In addition to the distal end of the probe 110, the multiple coils 130 may be placed apart in the lengthwise direction of the probe 110 between the distal end and the proximal end. Thereby, it is possible to deliver magnetic stimulation to multiple target sites concurrently through one inserted probe 110.

Furthermore, the coils 130 placed at each location on the probe 110 may be placed at various angles. For example, each coil 130 placed at different locations may be selectively placed such that its axial direction is parallel or perpendicular to the insertion direction of the probe 110. By appropriately placing the coils 130 on the probe 110 in consideration of target sites for insertion and stimulation range of the corresponding target sites, it is possible to deliver magnetic stimulation of various ranges and directions with one probe 110.

On the other hand, as shown in FIGS. 2 and 3, in case that a single coil 130 is used, a magnetic field is formed outside the coil 130, and thus focality at the target site is not relatively high.

In view of this, when a pair of coils 130 is placed close to each other at a location on the probe 110 to make a pair, each magnetic field by the pair of coils 130 reinforce each other at the target site, thereby increasing the focality of the magnetic field at the target site.

Figure 4:
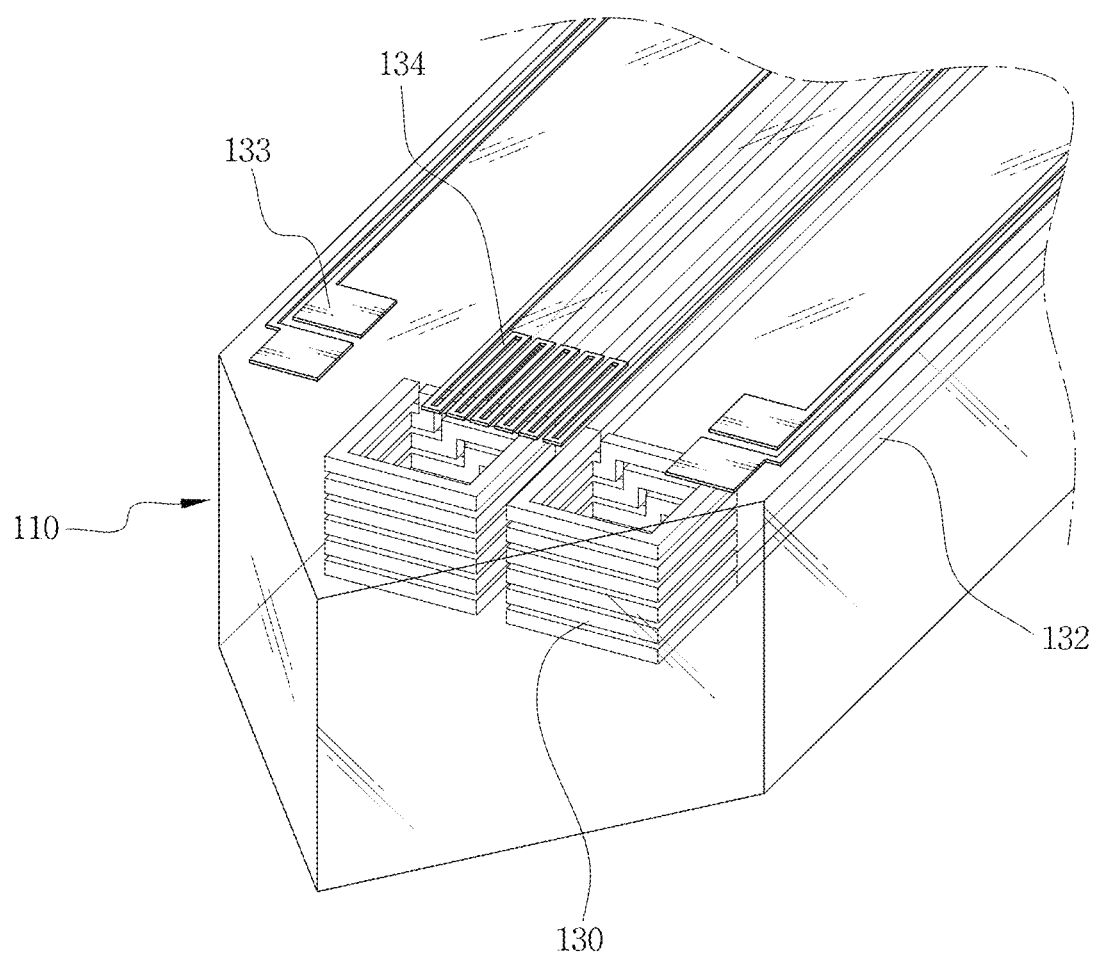
FIG. 4 is a partially enlarged perspective view schematically showing an example of a neural probe structure with two coils placed perpendicular to an insertion direction of a probe.
Figure 5:
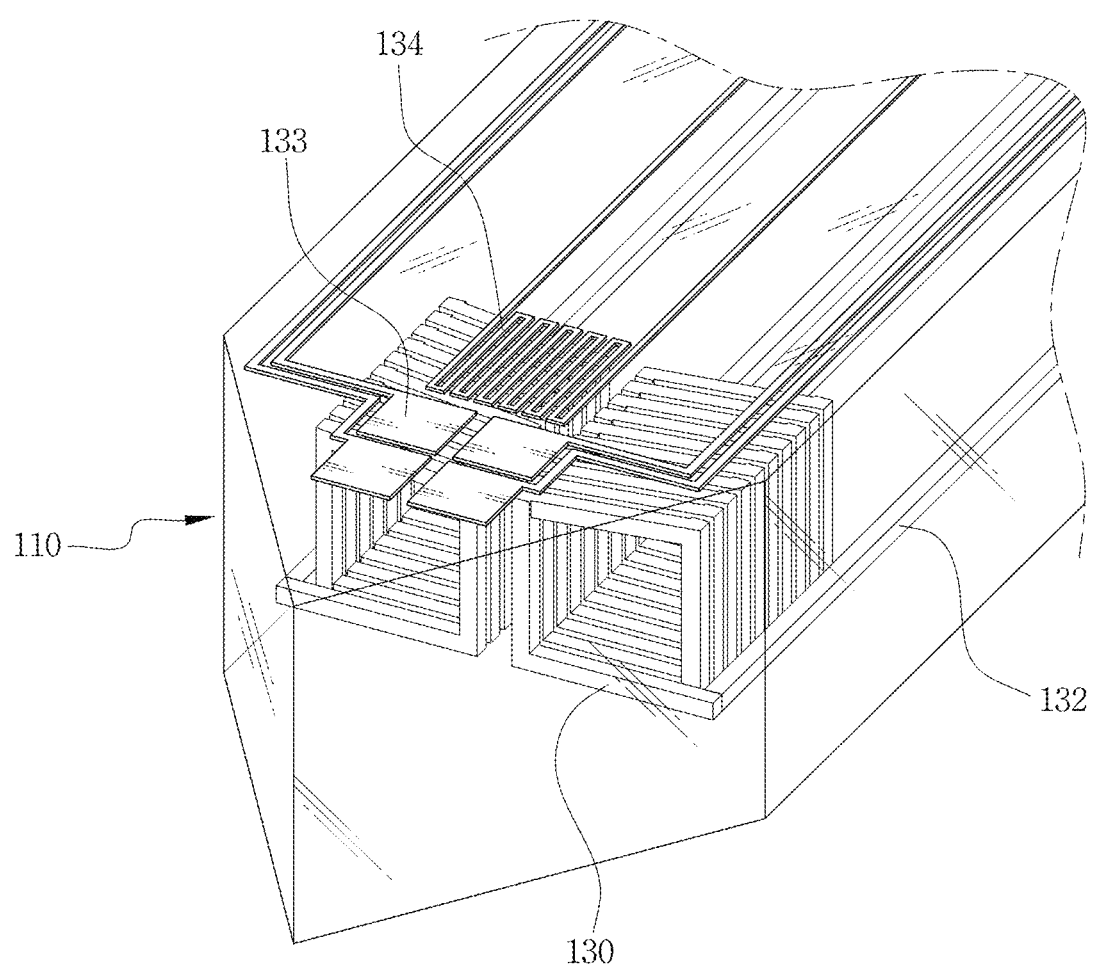
FIG. 5 is a partially enlarged perspective view schematically showing an example of a neural probe structure with two coils placed parallel to an insertion direction of a probe.

Referring to FIGS. 4 and 5, when the pair of coils 130 are placed such that each axial direction is parallel to each other, and an electric current is allowed to flow such that the directions of each magnetic field face the opposite directions with respect to the axial direction, the magnetic fields can reinforce each other at the target site in front of the open end of the pair of coils 130, and the magnetic fields can cancel out each other at the remaining site. Thereby, focality of the magnetic stimulation at the target site can be increased. In this instance, the magnetic field of stronger strength is intensively formed between the coils 130, and the magnetic fields formed by each coil 130 in the remaining range are cancelled because of the opposite directions of the magnetic fields. Accordingly, when the probe 110 is inserted such that the target site is disposed between the two coils 130, magnetic stimulation can be intensively delivered to the target site, and the magnetic field applied to the remaining site can be minimized.

Figure 6:
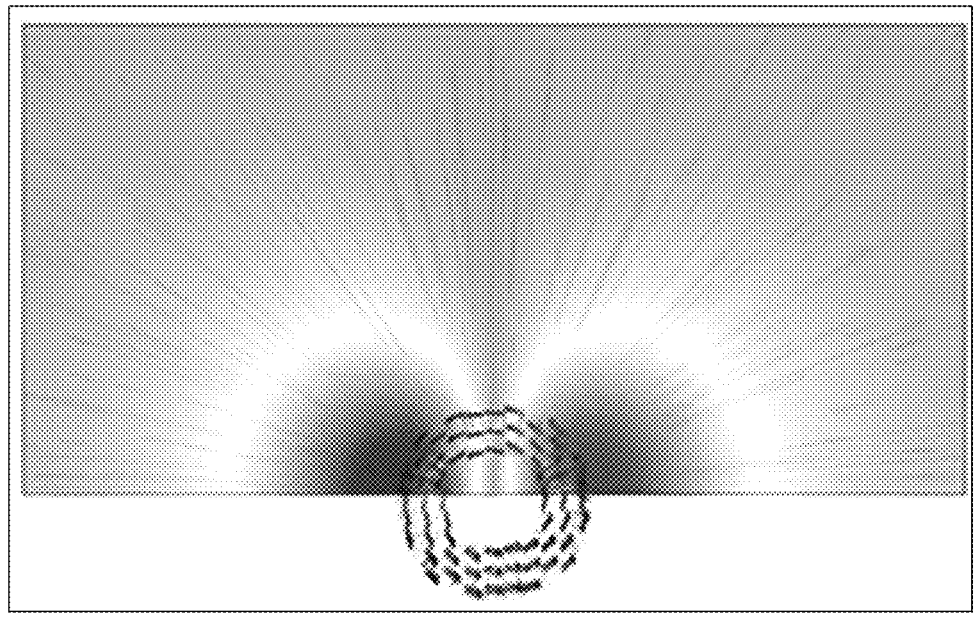
FIG. 6 shows a magnetic field distribution around a coil in case that the number of coils used is one.
Figure 7:
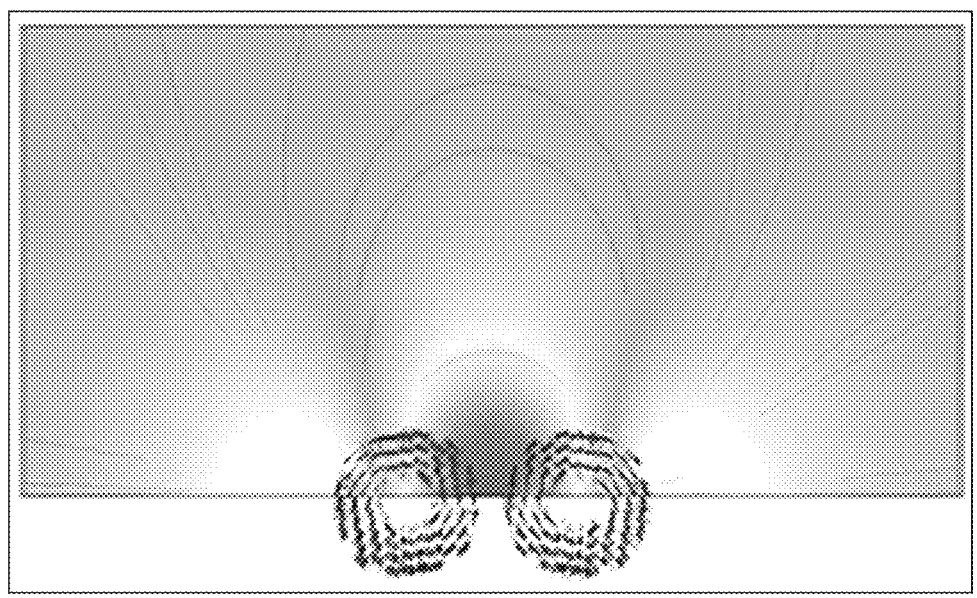
FIG. 7 shows a magnetic field distribution around a coil in case that the number of coils used is two.

Referring to FIG. 6, in the case of the single coil 130, it could be seen that the magnetic field was formed over a wide range around the coil 130. However, in case that the coils 130 placed such that the directions of each magnetic field face the opposite directions were used, the magnetic fields were intensively formed at the target site as shown in FIG. 7.

On the other hand, in case that magnetic fields are formed in the same direction in each coil 130 whose axial directions are arranged parallel to each other, as a result, the same effect as a large single coil 130 could be obtained.

Although not shown, by placing a plurality of adjacent coils 130 each at various angles, it is possible to form magnetic fields of various strengths and ranges using reinforcement and cancellation of each magnetic field.

Two pairs of coils 130 may be placed at two different locations of the probe 110. For example, as shown in FIG. 1, one pair of coils 130 may be placed at the distal end of the probe 110, and the other pair of coils 130 may be placed between the distal end and the proximal end of the probe 110. More pairs of coils 130 may be placed at multiple locations of the probe 110.

Furthermore, each pair of coils 130 placed at different locations may be selectively placed such that the axial direction is parallel to the insertion direction of the probe 110 or perpendicular to the insertion direction of the probe 110.

On the other hand, the coil 130 may be a coil with various shapes including a circular shape and a rectangular shape. Rather, when considering the present disclosure is manufactured to a small scale, a rectangular coil as shown in each drawing is advantageous to the coil 130. A method for manufacturing the coil 130 is described in detail below.

As described above, localized magnetic stimulation can be delivered to a target site at a high depth through the coil 130 embedded in the probe 110, and it is possible to deliver magnetic stimulation at various angles and intensities, and deliver stimulation to multiple target sites at the same time.

On the other hand, the coil 130 may be supplied with an external power source through a power transmitting-receiving electrode 131 on the body 120. The power transmitting-receiving electrode 131 and the coil 130 are electrically connected through a power transmitting-receiving line 132 formed in the probe 110.

An electrode array 133 may be provided at the distal end of the probe 110 to obtain neural signals emitted from the target site in response to the magnetic stimulation by the coil 130. The signals obtained through the electrode array 133 are transmitted to the power transmitting-receiving electrode 131 on the body 120 side through the power transmitting-receiving line 132. The transmitted signals are transmitted to an external analysis means, thereby to analyze changes of the target site caused by the magnetic stimulation.

On the other hand, an electric current may be supplied to the electrode array 133 to stimulate the target site with electricity. Also, the electrode array 133 may sense the neural signal caused by the stimulation. That is, it is possible to stimulate the target site with electricity, and to subsequently sense the neural signal through the same electrode array 133.

The electrode array 133 is placed such that the coil 130 and the electrode array 133 do not overlap when viewed in the axial direction of the coil 130, to prevent the magnetic field interference of the coil 130 caused by the electrode array 133. Preferably, the electrode array 133 is placed at the probe 110 such that the target site is not hidden by the electrode array 133 when viewed from the coil 130.

In the case of the horizontal coil 130 as shown in FIGS. 3 and 5, as the influence is relatively low, the electrode array 133 may be concentrated at the center. However, in the case of the vertical coil 130 as shown in FIGS. 2 and 4, if the electrode array 133 is placed at the center, the electrode array 133 is disposed on the open end where the strength of the magnetic field of the coil 130 is strongest, so it is preferred that the electrode array 133 is placed at each of the two sides.

On the other hand, when the multiple coils 130 are placed on the probe 110 apart from each other in the lengthwise direction, the electrode array 133 may be placed for each coil 130, and the electrode array 133 may be placed near only some coils 130. In case that the electrode array 133 is placed at only some coils 130, the neural signals from the individual sites to which magnetic stimulation is applied by each coil 130 allow the identification of the corresponding site, taking into account the time when the signals are generated and received.

When an electric current is supplied to the coil 130 for magnetic stimulation, heat may be generated in the probe 110. Accordingly, a temperature sensor array 134 is placed at a location on the probe 110 adjacent to the coil 130 to measure the temperature in the body in real time, and to stop the magnetic stimulation when the probe 110 is heated beyond an optimal temperature, thereby increasing stability.

The neural probe structure 100 according to the present disclosure may further include stimulation means such as fluid stimulation and optical stimulation to perform various types of neural stimulation simultaneously.

Below is a description of a method for manufacturing the neural probe structure 100 described above. A method of assuming the shape of the probe 110 and the body 120, and forming electrodes on the probe 110 and the body 120 may use known technique, and a method of embedding the vertical and horizontal coil 130 in the microscale probe 110 is mainly described in the specification.

The neural probe structure 100 according to an embodiment of the present disclosure is manufactured by stacking a plurality of layers including the probe 110, the coil 130 and the power transmitting-receiving line 132 through a photo resist. In the following description, the probe 110 is made from polymer material, however, in an alternative embodiment, the probe 110 may also be made from $SiO_2$, $Si_3N_4$, or other insulating blends. The coil 130 and the power transmitting-receiving line 132 may be made of a conducting metal material.

FIGS. 8A to 8G show the state of the neural probe structure 100 at each step for manufacturing the neural probe structure 100 having the vertical coil 130. On the other hand, it should be noted that only the coil 130 and the power transmitting-receiving line 132 are shown and the substrates that make up the probe 110 are omitted for convenience of description. Particularly, it should be understood that a dotted line represents a pattern on a lower substrate hidden by a substrate stacked thereon.

Figure 8A:
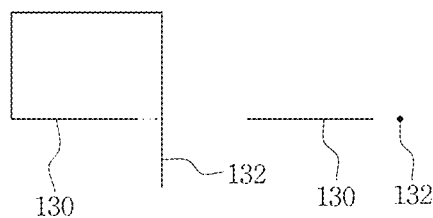
FIGS. 8A to 8G are schematic plane and side views showing the state at each step according to a method for manufacturing the neural probe structure of FIG. 2.

First, as shown in FIG. 8A, a first turn of an open loop type forming the coil 130 and the power transmitting-receiving line 132 connected thereto are deposited on a first pattern formed on a first substrate comprising the bottom of the probe 110, to fill the first pattern with a conductor. In this instance, the first turn has a cut-out part and is not completely continuous as shown.

Figure 8B:
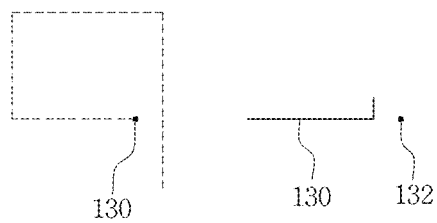

Subsequently, as shown in FIG. 8B, a second substrate including a pillar extending upwards from one end of the first turn of the coil 130 is further stacked on the first substrate. The first turn and the pillar are electrically connected.

Figure 8C:
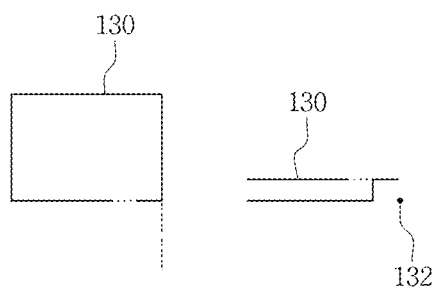

Subsequently, as shown in FIG. 8C, a third substrate is stacked on the second substrate, the third substrate including a second turn placed adjacent to and parallel to the first turn of the coil 130 and the remainder portion completed with polymer material. Thereby, the first turn and the second turn of the coil 130 are electrically connected with the pillar. In this instance, the added second turn extends from the top of the pillar and is not completely continuous with its cut-out part.

Figure 8D:
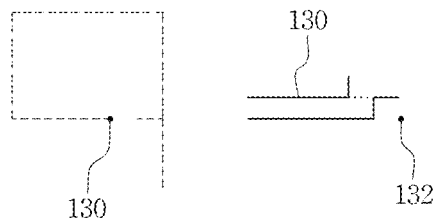

Subsequently, as shown in FIG. 8D, another substrate is further stacked, including a pillar electrically connecting the second turn formed at the step of FIG. 8C to an adjacent third turn that will be formed later and the remainder portion completed with polymer material.

Figure 8E:
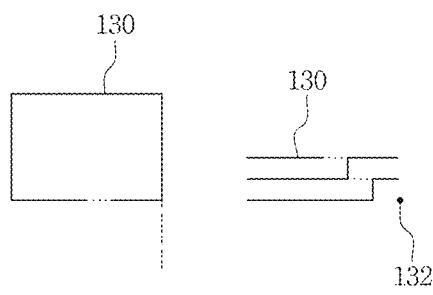
Figure 8F:
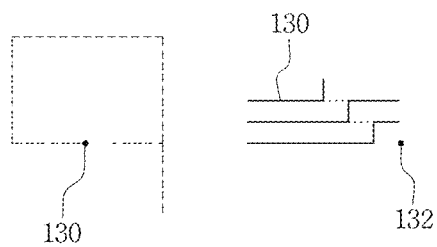

Subsequently, as shown in FIGS. 8E and 8F, the previous step is iteratively performed to manufacture the coil with a necessary number of turns. That is, one or more substrates including one of the remaining turns of the coil 130 of an open loop type and pillars electrically connecting each turn in an alternating manner are stacked in a sequential order, to manufacture a probe comprising a coil of multiple turns embedded therein.

Figure 8G:
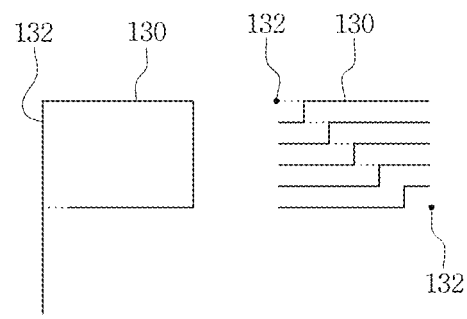

Finally, as shown in FIG. 8G, a top substrate is stacked, in which the topmost turn of the coil 130 and the power transmitting-receiving line 132 connected thereto are deposited. Subsequently, although not shown, the power transmitting-receiving electrode 131 is formed to complete a circuit connected to the coil 130.

The probe 110 and the body 120 having the circuit are patterned and released to complete the neural probe structure 100 including the vertical coil 130 according to an embodiment of the present disclosure.

Figure 9A:
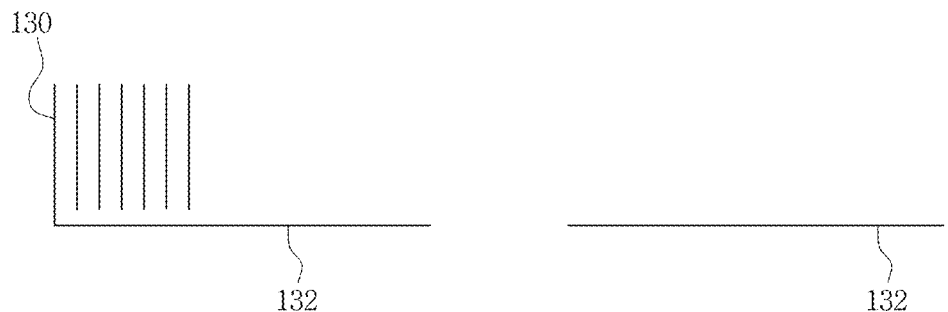
FIGS. 9A to 9C are schematic plane and side views showing the state at each step according to a method for manufacturing the neural probe structure of FIG. 3.
Figure 9B:
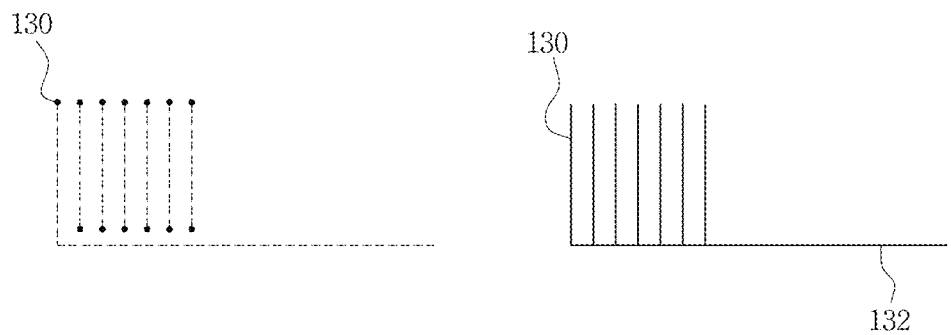
Figure 9C:
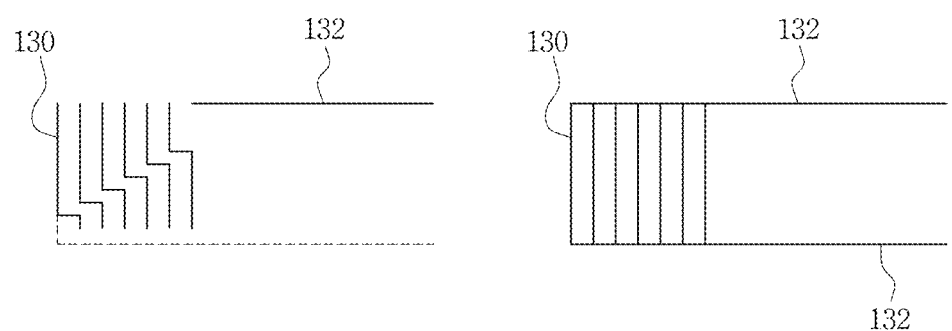

FIGS. 9A and 9C show the state of the neural probe structure 100 at each step of manufacturing the neural probe structure 100 having the horizontal coil 130.

First, as shown in FIG. 9A, the base of each turn forming the coil 130 and the power transmitting-receiving line 132 connected thereto are deposited on a polymer substrate comprising the bottom of the probe 110 to form a first substrate. In this instance, the remaining turns except the foremost turn of the coil 130 are formed such that they are isolated from the power transmitting-receiving line 132 as shown.

Subsequently, as shown in FIG. 9B, a second substrate is stacked on the first substrate, the second substrate including pillars each extending upwards from two ends of the base of each turn forming the coil 130. In the case of the foremost turn of the coil 130, a pillar is only formed on a side that is not connected to the power transmitting-receiving line 132.

Finally, the pillars of each turn forming the coil 130 and the power transmitting-receiving line 132 connected thereto are deposited to form a third substrate. The pillar of the foremost turn of the coil 130 is connected to the opposite turn to the adjacent turn. The remaining pillar of the adjacent turn is connected to the opposite turn to the adjacent turn again. That is, as shown in FIG. 9C, a third substrate is stacked on the second substrate, the third substrate including the top surface of each turn of the coil 130 connecting one side pillar of one turn of two adjacent turns to the other side pillar of the other turn. Subsequently, although not shown, the power transmitting-receiving electrode 131 is formed to complete a circuit connected to the coil 130.

The probe 110 and the body 120 having the circuit is patterned and separated to complete the neural probe structure 100 including the horizontal coil 130 according to an embodiment of the present disclosure.

As described above, the rectangular coil 130 is manufactured by a stacking method using a photo resist, thereby manufacturing a neural probe structure with high yield. Particularly, in the case of a general coil, the height continuously increases with the increasing number of turns, for example, in a spiral shape, but the rectangular coil in this example can be easily manufactured by a stacking method having a uniform thickness with a discontinuously increasing height due to the steps.

Although the embodiments of the present disclosure have been hereinabove described in further detail with reference to the accompanying drawings, the present disclosure is not necessarily limited to these embodiments, and modifications may be made to the embodiments in various forms without departing from the technical spirit of the present disclosure.

Accordingly, the embodiments disclosed in the present disclosure are provided to describe the technical spirit of the present disclosure, but not intended to limit, and the scope of the technical spirit of the present disclosure is not limited by these embodiments. Therefore, it should be understood that the embodiments described hereinabove are illustrative, but are not limitative, in all aspects. The scope of protection of the present disclosure should be interpreted by the appended claims, and the full technical spirit within the scope in equivalence thereto shall be interpreted as being included in the scope of protection of the present disclosure.

What is claimed is:

1. A neural probe structure comprising:
   a probe configured to be insertable in a length direction into a living body; and
   a magnetic field inductor disposed in the probe,
   wherein the magnetic field inductor is configured to generate a magnetic field adjustable to localize magnetic stimulation to a target site from the magnetic field,
   wherein the magnetic field inductor is a rectangular coil.

2. The neural probe structure according to claim 1, wherein the coil is configured such that a magnetic axis of the coil is parallel to a length of the probe.

3. The neural probe structure according to claim 1, wherein the coil is configured such that a magnetic axis of the coil is perpendicular to a length of the probe.

4. The neural probe structure according to claim 1, further comprising an additional one or more magnetic field inductors disposed at one or more intervals along a length of the probe.

5. The neural probe structure according to claim 4, wherein the neural probe is configured to generate a plurality of magnetic fields adjustable to localize magnetic stimulation at a corresponding plurality of target sites using the additional one or more magnetic field inductors.

6. The neural probe structure according to claim 5, wherein the neural probe is configured to simultaneously stimulate the corresponding plurality of target sites.

7. The neural probe structure according to claim 1, wherein an electrode array is disposed in the probe and configured to obtain a neural signal generated in response to the magnetic stimulation.

8. The neural probe structure according to claim 1, wherein the probe includes a temperature sensor array configured to measure temperature at the target site.

9. The neural probe structure according to claim 8, wherein the probe is configured to limit magnetic stimulation based on the temperature measured by the temperature sensor array.

10. The neural probe structure according to claim 1, wherein the magnetic field is adjustable to localize magnetic stimulation to the target site by controlling one or more of a strength of the magnetic field, a range of the magnetic field, and a direction of the magnetic field.

11. A probe structure comprising:
    a probe configured to be insertable in a length direction into a living body; and
    a pair of magnetic field inductors disposed in the probe and configured to generate a respective pair of magnetic fields such that a strength of a resultant magnetic field is increased by constructive interference at a target site of the probe.

12. The probe structure according to claim 11, wherein the pair of magnetic field inductors are a pair of coils, each coil having a magnetic axis parallel to the other, and
    wherein the pair of coils are configured to generate a pair of magnetic fields opposite to each other in direction.

13. The probe structure according to claim 11, wherein the pair of magnetic field inductors comprises a first coil that is wound in a first direction about a first magnetic axis and a second coil that is wound in a second direction about a second magnetic axis, wherein the first direction and the second direction are opposite and the first magnetic axis and the second magnetic axis are parallel.

14. A method for manufacturing a neural probe structure, the method comprising:

forming a first pattern on a first substrate, and filling the first pattern with a first conductor;

stacking a second substrate on the first substrate; and forming a second pattern connected to the first pattern on the second substrate, and filling the second pattern with a second conductor, wherein the first substrate and the second substrate form a probe configured to be insertable in a length direction into a living body, and wherein the first conductor of the first pattern and the second conductor of the second pattern form a magnetic field inductor disposed in the probe and configured to generate a magnetic field adjustable to localize magnetic stimulation to a target site from the magnetic field.

15. The method for manufacturing according to claim 14, wherein the magnetic field inductor is formed in a shape of a coil.

16. The method for manufacturing according to claim 15, wherein the first conductor of the first pattern is a first turn of the coil of an open loop type, the second conductor of the second pattern is a pillar extending upwards from one end of the first turn, and the method further comprises stacking additional one or more substrates including one of remaining turns of the coil of an open loop type and additional pillars electrically connecting each turn in an alternating manner on the second substrate in a sequential order, to form the coil having a magnetic axis perpendicular to a length of the probe.

17. The method for manufacturing according to claim 15, wherein the first conductor of the first pattern comprises a plurality of conductive lengths that form a first quarter-turn part of the coil, the second conductor of the second pattern comprises pillars each extending upwards from the plurality of conductive lengths to form a second quarter-turn part of the coil and to form a fourth quarter-turn part of the coil, the second quarter-turn part facing the fourth quarter-turn part, and the method further comprises stacking on the second substrate a third substrate comprising a third conductor that forms a third quarter-turn part of the coil, such that the first, second, third, and fourth quarter-turn parts collectively form the coil having a magnetic axis parallel to a length of the probe.

\* \* \* \* \*